United States Patent [19]

Danforth

[11] Patent Number: 4,909,787
[45] Date of Patent: Mar. 20, 1990

[54] CONTROLLABLE FLEXIBILITY CATHETER WITH ECCENTRIC STIFFENER

[76] Inventor: John W. Danforth, 875 25th Ave., San Francisco, Calif. 94121

[21] Appl. No.: 231,625

[22] Filed: Aug. 11, 1988

Related U.S. Application Data

[63] Continuation of Ser. No. 91,234, Aug. 31, 1987, abandoned, which is a continuation-in-part of Ser. No. 896,471, Aug. 14, 1986, abandoned.

[51] Int. Cl.⁴ ............................................. A61M 25/00
[52] U.S. Cl. .................................................... 604/95; 604/282; 606/194
[58] Field of Search ............................ 128/344, 348.1; 604/95–103, 280–282

[56] References Cited

U.S. PATENT DOCUMENTS

| | | | |
|---|---|---|---|
| 1,060,665 | 5/1913 | Bell | 604/281 |
| 2,548,602 | 4/1951 | Greenburg | 128/344 |
| 3,021,834 | 2/1962 | Sheldon | 128/6 |
| 3,470,876 | 10/1969 | Barchilon | 604/95 |
| 3,769,981 | 11/1973 | McWhorter | 604/96 |
| 3,773,034 | 11/1973 | Burns et al. | 604/95 X |
| 4,033,331 | 7/1977 | Guss et al. | 604/95 X |
| 4,141,364 | 2/1979 | Schultze | 128/344 X |
| 4,195,637 | 4/1980 | Gruntzig et al. | 128/348.1 |
| 4,215,703 | 8/1980 | Willson | 128/772 |
| 4,248,234 | 2/1981 | Assenza et al. | 604/282 |
| 4,498,473 | 2/1985 | Gereg | 604/281 |
| 4,573,470 | 3/1986 | Samson et al. | 128/344 |
| 4,582,181 | 4/1986 | Samson | 128/348.1 |
| 4,586,923 | 5/1986 | Gould et al. | 604/95 |
| 4,601,705 | 7/1986 | McCoy | 604/95 |
| 4,616,652 | 10/1986 | Simpson | 604/344 |
| 4,662,404 | 5/1987 | LeVeen et al. | 128/348.1 |
| 4,685,473 | 8/1987 | Karcher et al. | 604/95 X |

FOREIGN PATENT DOCUMENTS 2044109  10/1980  United Kingdom .

*Primary Examiner*—Dalton L. Truluck
*Attorney, Agent, or Firm*—Townsend and Townsend

[57] ABSTRACT

A guiding catheter 20 of variable, operator-controlled flexibility to be used in the performance of a percutaneous translumenal coronary angioplasty procedure is described which includes an elongate housing 42 suitable for insertion into an artery, as well as an operator-controlled variable stiffener coupled to the distal aspect of the catheter to permit the operator performing the angioplasty procedure to increase the rigidity of the catheter. In a preferred embodiment the stiffening apparatus consists of a fluid-filled chamber eccentrically displaced along the longitudinal axis of the catheter housing nearly encompassing the housing that contains a segment capable of asymmetric elongation when subjected to hydrostatic pressure resulting in the development of torque and increased rigidity of the distal end as desired by the operator. Increasing the rigidity of the guiding catheter, once installed within the coronary ostium, precludes disengagement of the guiding catheter, thus expediting the performance and enhancing the safety of the procedure.

24 Claims, 6 Drawing Sheets

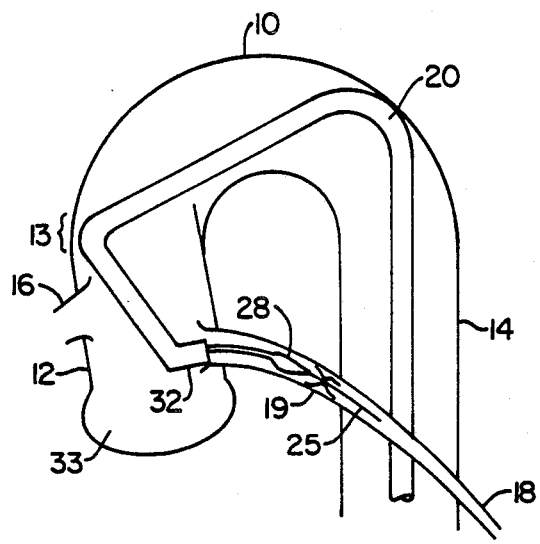
FIG.\_1.
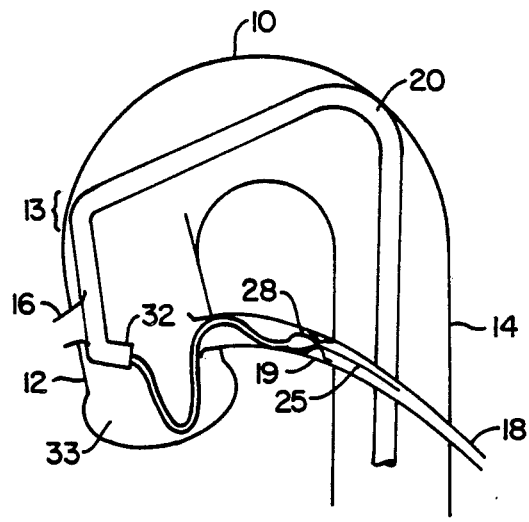
FIG.\_2.

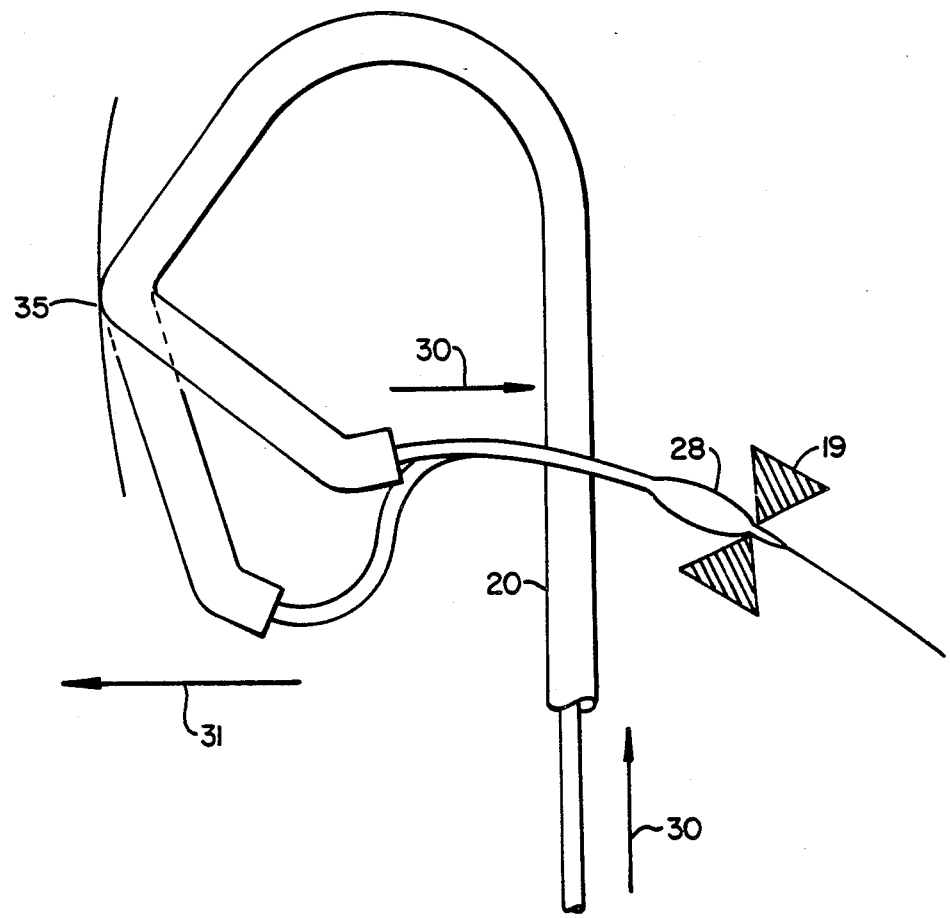
FIG._3.

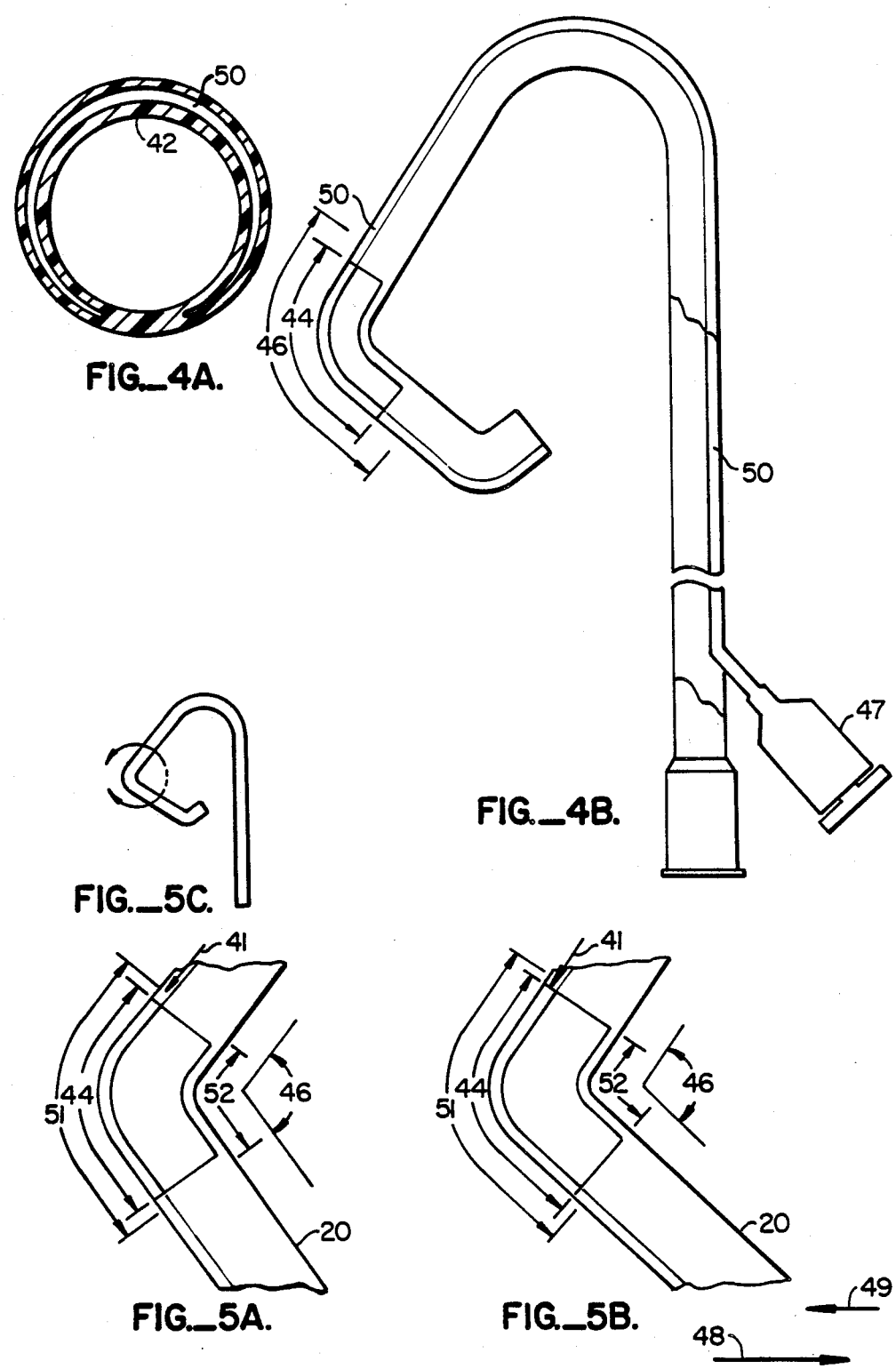

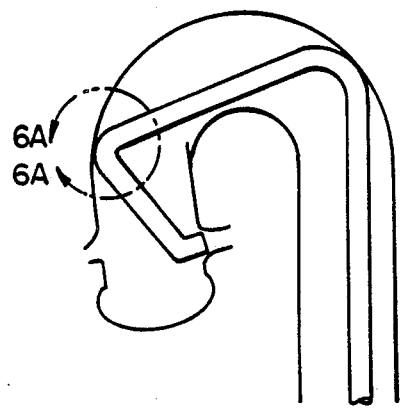
FIG._6.
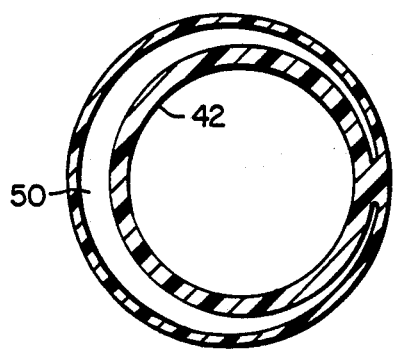
FIG._6E.
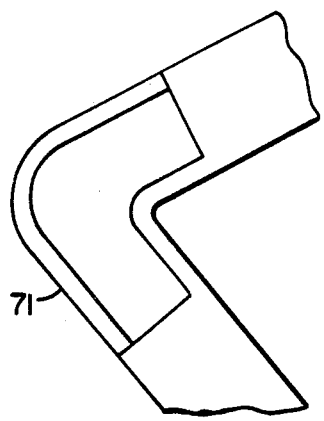
FIG._6A.
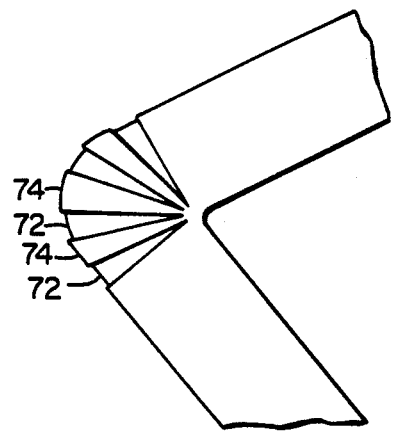
FIG._6B.
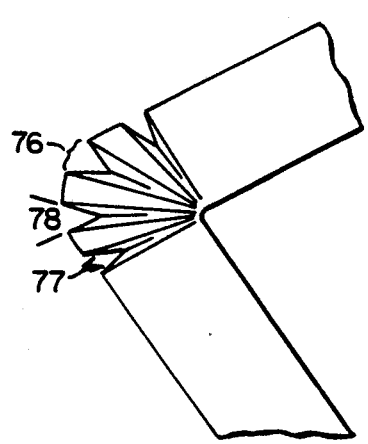
FIG._6C.
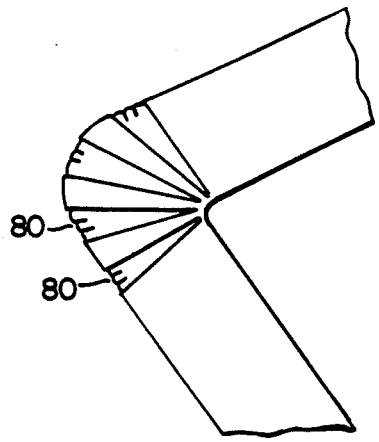
FIG._6D.

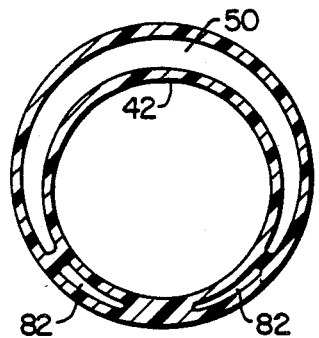
FIG._7A.
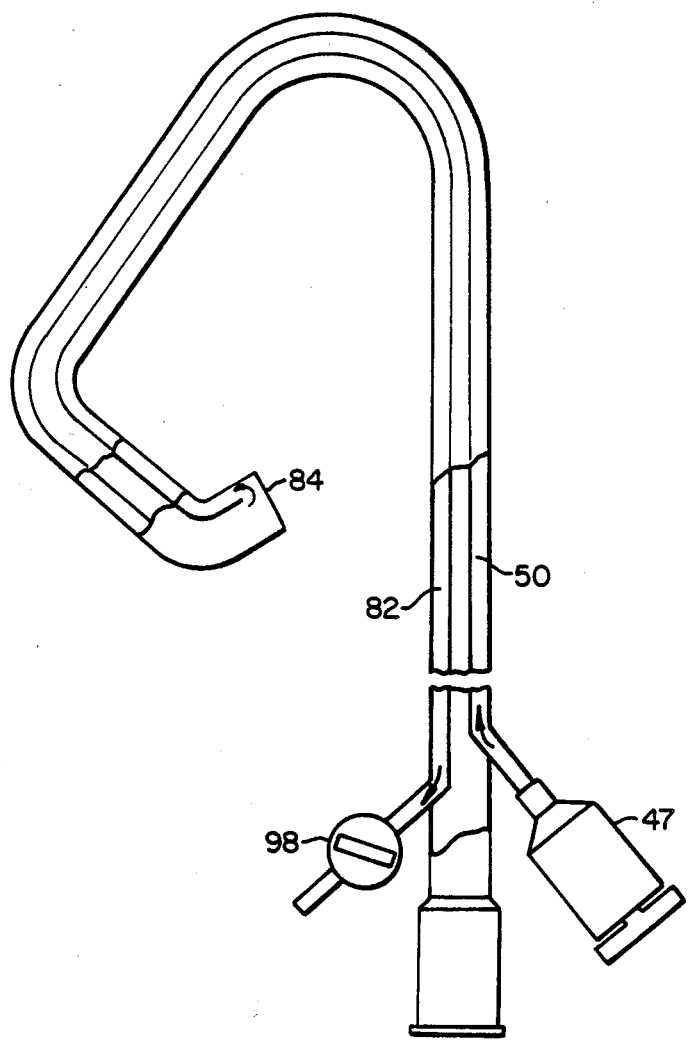
FIG._7B.

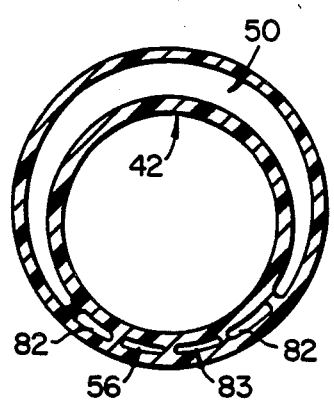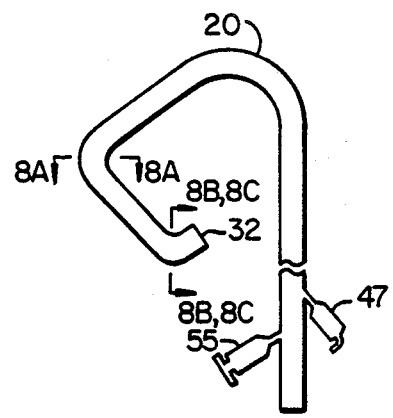
FIG._8A.
FIG._8.
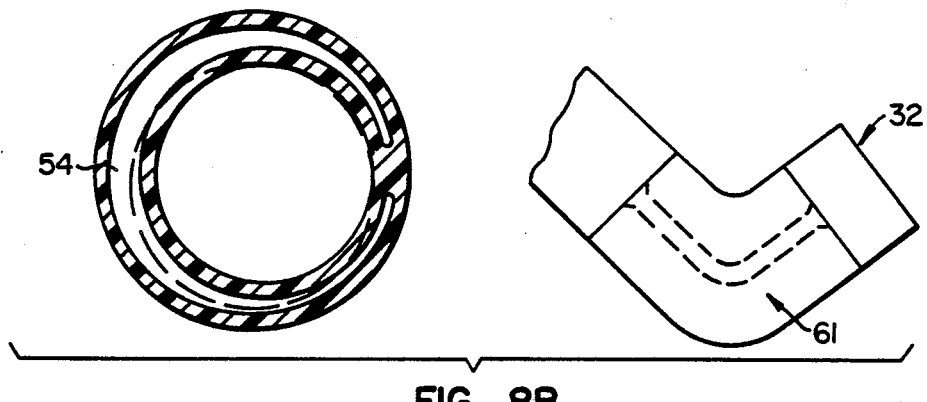
FIG._8B.
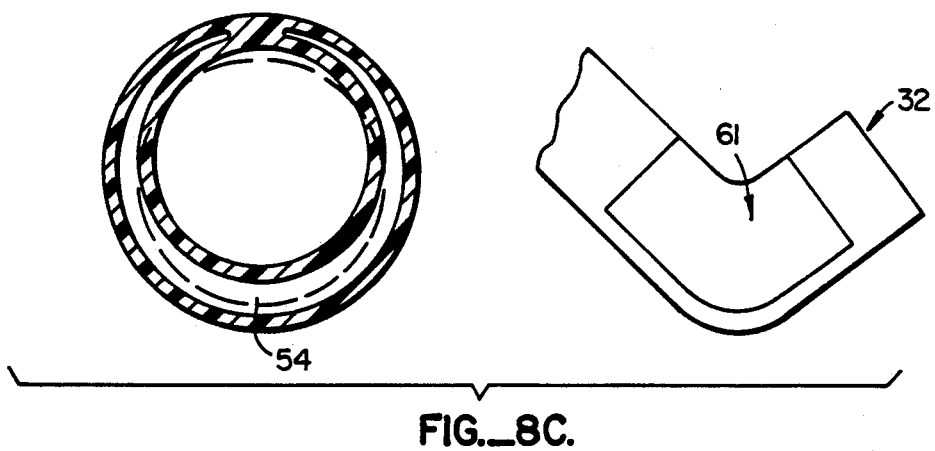
FIG._8C.

CONTROLLABLE FLEXIBILITY CATHETER WITH ECCENTRIC STIFFENER

REFERENCE TO RELATED APPLICATION

This is a continuation of application Ser. No. 07/091,234, filed Aug. 31, 1987, now abandoned.

Which application is a continuation-in-part of U.S. patent application Ser. No. 896,471, filed Aug. 14, 1986, and now abandoned, and entitled "Controllable Flexibility Catheter."

BACKGROUND OF THE INVENTION

1. Field of the Invention

This invention relates to catheters, and in particular, to a guiding catheter to be used in the performance of a percutaneous translumenal coronary intervention (balloon angioplasty, laser angioplasty, angioscopy or atherectomy), and in particular to a guiding catheter which provides variable operator adjusted flexibility and torque control.

2. Description of the Prior Art

In 1977 Andreas Grüntzig first used a balloon-tipped flexible catheter to percutaneously dilate a region of stenosis within the coronary artery of a patient with atherosclerotic coronary artery disease. Since that time, the incidence of percutaneous translumenal coronary angioplasty (herein sometimes PTCA) has increased exponentially. In the last several years, the performance of this procedure has become routine within most major medical centers throughout the world. Furthermore, with the advent of improved technology and increased operator skill, the indications for this procedure have also substantially increased.

Concurrent with the aggressive utilization of this technique, physicians with expertise in angioplasty have been approaching increasingly difficult lesions percutaneously, and physicians with relatively little experience in angioplasty have been attempting to dilate relatively straightforward lesions with minimal formal training. With the advent of new technology, it is likely that other procedures including laser angioplasty, angioscopy and intra-coronary atherectomy will similarly become routine. Although it is acknowledged that the guiding catheter described herein will have application to these procedures as well, for the purpose of clarity the balance of this discussion will be confined to the application of the guiding catheter to the performance of percutanous transluminal balloon coronary angioplasty.

In a routine angioplasty procedure using conventional catheters, a preshaped semi-rigid guiding catheter is introduced into a peripheral artery, advanced over a guidewire along the course of the aorta and subsequently engaged within the appropriate coronary ostium. Once engaged, a second catheter (an angioplasty balloon dilation catheter), equipped with a balloon at its distal aspect and a flexible steerable intra-coronary guidewire, is introduced within the guiding catheter and advanced to within the distal aspect of the guiding catheter. The intra-coronary guidewire then is advanced within the lumen of the diseased vessel and manipulated across the region of stenosis. By rotating the guidewire, which contains a slight bend, the operator can control the course of the wire and select the appropriate lumen. Once the guidewire is positioned across the region of stenosis, the operator advances the dilation balloon over the guidewire and positions it across the stenotic lesion. The angioplasty then is accomplished by inflating the balloon to about 6–10 atmospheres of pressure. Usually three to four dilations are required for each region of stenosis, with the duration of each dilation varying between 30 to 90 seconds, depending upon anatomic considerations and operator preference Following the final dilation, the guidewire and angioplasty balloon are withdrawn, leaving the guiding catheter in place. Coronary angiography may then be performed to evaluate the appearance of the vessel following the procedure and to determine the severity of any residual stenosis.

There are several major obstacles to the successful performance of an angioplasty procedure. One major difficulty involves manipulation of the dilation balloon catheter across the region of stenosis within the appropriate coronary artery. Although the guidewire can frequently be advanced across the region with relative ease, manipulation of the balloon across the stenosis is frequently more difficult because the deflated cross-sectional profile of the dilation balloon catheter is considerably larger than the corresponding profile of the guidewire. Hence, relatively more resistance to the passage of this catheter within the coronary artery is commonly incurred. Merely advancing the angioplasty dilation balloon catheter against this resistance often results in disengagement of the guiding catheter from the coronary ostium. Once this disengagement occurs, the angioplasty dilation balloon catheter frequently prolapses within the ascending aorta, precluding further advancement of this catheter.

Inability to advance the angioplasty balloon across the coronary stenosis because of instability of the guiding catheter and subsequent prolapse of the angioplasty balloon catheter represents one of the most common reasons for failure during the performance of a coronary angioplasty procedure. The guiding catheter disengages in this circumstance because of its flexibility. The guiding catheter has intrinsic flexibility because it must conform to the configuration of the aorta and aortic arch, which contain both linear and curved segments, during introduction. Insertion of the guiding catheter requires that it be advanced over a guidewire up the aorta, which is relatively straight, and then over the aortic arch, which, as the name implies, is curvilinear.

The only stability afforded by guiding catheters of the prior art relates to the limited intrinsic stiffness of these catheters. The stiffness of these prior art guiding catheters is subject to a "warm-up" phenomenon (becoming more flexible as they remain in the body and equilibrate to body temperature) and thus varies inversely with the temperature of the device. Hence, these catheters tend to be particularly stiff on introduction into the boy, when flexibility is preferable, and yet relatively flexible and hence unstable following exposure to body temperatures during balloon catheter manipulation across a coronary stenosis when rigidity is preferable.

Efforts to prevent disengagement of the guiding catheters of the prior art have focused upon the development of dilation balloon catheters designed to produce less resistance during manipulation across a stenotic lesion. It was originally proposed that these "low resistance" angioplasty dilation catheters would produce less "back pressure" during manipulation across a coronary stenosis and in this way preclude disengagement of the guiding catheter. Several approaches were pursued to minimize the resistance characteristics of these balloon catheters including the development of lower profile balloons (when deflated), lubricious balloons and smooth tapered tips. By themselves, however, these approaches did not circumvent the problem. For example, despite extensive research and development, the cross-sectional diameter of the lowest profile dilation catheter currently available is considerably greater than the corresponding diameter of the guidewires used in conventional coronary angioplasty. Hence, the resistance generated during the passage of these "low resistance" balloon dilitation catheters across stenotic lesions remains a problem. These smaller catheters do not permit reliable transmission of intra-coronary pressures and, for this reason, their use obscures vital intra-coronary hemodynamic monitoring on frequent occasions. Additionally, the caliber of these low profile balloons, when inflated, is substantially smaller than the corresponding caliber of most conventional angioplasty catheters. Thus, their use frequently necessitates the installation of an intracoronary exchange wire as well as the introduction of a second (larger caliber) angioplasty dilation balloon catheter. The use of this second dilation catheter, and the necessary exchange wire, frequently increases the duration, expense, complexity and ultimate complication rate of the procedure.

In the prior art, dislodgement of the guiding catheter was prevented either by forcing the guiding catheter down the course of the vessel to be dilated or by bending the guiding catheter in such a way that it "banked" off the back wall of the aorta before engaging the coronary ostium. Both of these techniques are particularly dangerous as they may result in dissection of the coronary artery proximal the region to be dilated.

SUMMARY OF THE INVENTION

I have developed a guiding catheter which overcomes the foregoing disadvantages of prior art catheters. My guiding catheter provides superior stability during the performance of an angioplasty relative to the prior art because it allows the operator to control both the flexibility of the distal aspect of the catheter as well as the torque provided by this portion of the catheter. This feature permits the operator to select the compliance characteristics most suitable for each phase of the procedure. For example, during introduction the catheter is made more flexible to facilitate advancement over the guidewire within the aorta an engagement within the coronary ostia. Because the incidence of vascular trauma sustained during catheter introduction varies directly as a function of the relative stiffness of the catheter, this feature minimizes the potential for catheter-induced vascular trauma associated with the introduction of the catheter. Control of flexibility thus contribute to the safety of percutaneous intra-coronary procedures including coronary balloon angioplasty.

Following engagement, the catheter is made relatively inflexible to provide stability during the manipulation of the angioplasty dilation balloon catheter. The guiding catheter also permits the operator to generate considerable orque within the distal aspect of the catheter to preserve the engagement of the guiding catheter within the coronary ostium during manipulation of the dilitation balloon catheter. The enhanced stability afforded by the catheter circumvents the need to force the prior art relatively rigid guiding catheters deep within a coronary lumen to achieve stability, as well as the need for the sequential balloon technique. Thus, these features of the catheter contributes to the safety of the procedure during both guiding catheter introduction and balloon catheter manipulation.

In a preferred embodiment, my catheter includes an elongate housing member having an opening extending from a proximal end to a distal end, and controllable stiffening means consisting of an elongate primary chamber eccentrically disposed around the elongate housing to enable control of the flexibility of the catheter as well as the torque generated by the catheter. Optionally a second controllable stiffener may be employed to selectively deflect a distal segment of the catheter to more accurately align the catheter with the desired coronary artery ostium.

The catheter of my invention is easier to install in the body and engage within the desired coronary artery, while being less traumatic to the patient. It minimizes the time for the angioplasty and precludes, in many cases, the need for sequential dilitation balloon catheters and exchange wires.

BRIEF DESCRIPTION OF THE DRAWINGS

FIG. 1 is a schematic representation of a guiding catheter of the prior art engaged within the left main coronary artery illustrating the configuration of the guiding catheter prior to manipulation of the angioplasty dilitation balloon catheter across a region of the stenosis within the left anterior descending coronary artery;

FIG. 2 is a schematic representation similar to FIG. 1 illustrating one disadvantage of prior art guiding catheters, namely disengagement during manipulation of the dilation balloon catheter across the region of coronary stenosis;

FIG. 3 illustrates the forces which develop within the guiding catheter as the angioplasty dilation balloon catheter is advanced within (in this case) the left coronary artery, as well as the impact of these forces on the configuration of the guiding catheter;

FIG. 4 is a cross section of one embodiment of the catheter of my invention, together with a schematic sagittal section included for the purpose of orientation;

FIG. 5A, 5B, and 5C illustrates the means by which the catheter of my design functions to oppose the forces generated during manipulation of the dilitation balloon catheter;

FIGS. 6A-6D illustrate various alternate structures of the preferred embodiment;

FIG. 7 is a cross-sectional and longitudinal illustration of the preferred embddiment that depicts the venting system of the catheter; and FIG. 8 depicts several cross sections and longitudinal sections of the distal aspect of the catheter illustrating a means of deflecting the tip of the catheter to optimize coronary ostial engagement.

DETAILED DESCRIPTION OF THE PREFERRED EMBODIMENTS

FIG. 1 illustrates the typical configuration of a conventional left coronary guiding catheter in the aorta when engaged within the left main coronary artery during the performance of a left coronary artery 18 PTCA. (The guiding catheter has been drawn with a relatively large caliber for the purpose of clarity.) The aorta 10 includes an ascending portion 12 and a descending portion 14. The angioplasty dilation balloon 28 and intra-coronary guidewire 25 have been included in FIG. 1. Although a left Judkin's configuration guiding catheter is shown in this and subsequent illustrations, the invention is not confined to this configuration. My variably compliant guiding catheter can be applied to all configurations of guiding catheters including left and right Judkin's, Sone's, Stertzer and Amplatz configurations.

As described above, the performance of an angioplasty initially requires the introduction of a guiding catheter within a peripheral artery. By virtue of a guidewire (not shown) and the preshaped nature of guiding catheter 20 at its distal end 32, the catheter is manipulated up the descending aorta 14 and down the ascending aorta 12 to place the end 32 of the guiding catheter 20 within the coronar ostium, thus permitting subsequent advancement of the angioplasty guidewire 25 and balloon catheter 28 within the diseased vessel 18.

FIG. 2 illustrates a disadvantage of a guiding catheter of the prior art. The components depicted in FIG. 2 have been labeled with reference numerals corresponding to the components in FIG. 1. In FIG. 2 the dilation balloon 28 has been advanced to the region of stenosis 19. Because the resistance imparted by the lesion exceeds the compliance characteristics of the guiding catheter, however, further attempts to advance the balloon catheter result in disengagement of the guiding catheter 20 and prolapse of the balloon catheter.

In this circumstance, further attempts to advance the dilitation balloon catheter 28 across the region of stenosis 19 results in progressive destabilization of the system. This instability precludes the manipulation of the dilation balloon catheter 28 across the region of stenosis and thus, the successful completion of the angioplasty procedure. The instability of the guiding catheter is believed to result from several causes. The catheter itself has intrinsic flexibility to accommodate introduction. Also the material from which the catheter is manufactured (multiple layers of Dacron webbing coated with a plastic polymer) becomes more flexible as it warms to body temperature. Additionally, the configuration of the catheter provides little or no resistance to the forces which cause it to back out. For example, as shown in FIG. 3, the application of force 30 on the dilation balloon 28 to advance the dilation balloon across the region of stenosis increases the torque 31 on bend 35 in guiding catheter 20, causing the angioplasty balloon catheter 28 to prolapse in the ascending aorta precluding further progress.

FIGS. 4A and 4B illustrate one embodiment of the guiding catheter 20 of my invention. In contrast to prior art devices, the guiding catheter includes a means for varying the flexibility of the catheter as well as varying the torque generated within the distal aspect of the catheter at the option of the operator. For the embodiment shown in FIG. 4, these features are provided by a closed chamber 50 eccentrically disposed along almost the entire length of the housing 42 such that it virtually encompasses the housing. Chamber 50 may be filled with fluid. The channel preferably contains a relatively elastic segment 44 disposed preferentially along the outer circumference of the curvature 46 in the catheter. The hydrostatic pressure within channel 50 is adjusted as desired by the operator, for example, by use of a syringe 47 connected to channel 50 at the distal extracorporeal aspect of the catheter.

As shown by FIG. 5, the application of force to syringe 47 (not shown) results in the even distribution of hydrostatic pressure 41 within channel 50. Typically, the chamber will be designed to tolerate pressures on the order of 10 atmospheres. Because in one embodiment this channel contains a series of relatively flexible elastic segments 44 disposed along the circumferential surface 51 of the catheter in the region of curvature 46, surface 51 tends to elongate relative to the corresponding contra-lateral catheter surface 52 in response to the application of pressure in chamber 50, resulting in the development of torque 48 within the distal aspect of the catheter in the direction of the coronary ostium. In this circumstance the region 13 of the ascending aorta 12 (see FIGS. 1 and 2) functions as a fulcrum to support the catheter within the coronary ostium. The combination of the support afforded by the ascending aorta and the torque generated within the catheter by the pressure induced by syringe 47 oppose the force 49 generated during advancement of the dilitation balloon catheter and thus prevents disengagement of the guiding catheter. This enables the use of additional force to advance the dilation balloon 28 through the region of stenosis. Once the dilation balloon 28 has been advanced through the region of stenosis, the hydrostatic pressure within channel 50 is relieved, rendering the guiding catheter 20 substantially more flexible, and hence less likely to induce any intimal vascular damage. A pressure source is then applied to inflate tee balloon 28 of the dilation catheter (see FIG. 1) and thereby ablate the stenosis.

My invention offers several advantage over conventional guiding catheters used in the performance of an angioplasty procedure. Present catheters, in an effort to reach a compromise between flexibility and rigidity, are generally stiff, and therefore more difficult to advance within the aorta and engage within the ostium. My guiding catheter in its most flexible condition, permits easier engagement within the coronary ostium. Once engaged, the relative inflexibility of my catheter enables it to remain engaged within the ostium in a more stable manner than conventional catheters. This stability frequently precludes the need for multiple angioplasty catheters and exchange wires, with their associated disadvantages described above. By virtue of the controllable flexibility, the use of this catheter substantially eliminates the need to apply force to the coronary ostium and hence minimizes the trauma sustained by the patient during the course of the angioplasty. Disruption of the intima of the coronary ostium by conventional guiding catheters represents a well known complication of angioplasty procedures. This complication can result in a coronary occlusion, and hence, myocardial infarction. Finally, the compliance characteristics of my catheter are not affected by "warming up" to body temperature.

Because the catheter itself need not be as rigid as conventional catheters, the walls of the housing 42 need not be as thick. Accordingly, the caliber of the catheter may be less than the caliber of conventional guiding catheters. This feature permits insertion of the catheter within a smaller arteriotomy. Because the cross-sectional area of channel 50 is relatively large throughout nearly the entire length of the catheter, changes in hydrostatic pressure may be accomplished rapidly.

A further advantage of my catheter is that its use may preclude the normal requirement for two physicians. Two physicians typically are necessary, one to monitor the engagement of the guiding catheter, and one to advance the guidewire and balloon catheter. With my catheter, a physician may advance the catheter with one hand while adjusting the hydrostatic pressure within channel 50 with a syringe in the other hand, thus increasing and decreasing the rigidity of the, catheter as necessary to advance the dilitation catheter contained therein.

FIGS. 6A-6D illustrate alternative embodiments of my catheter. The various embodiments depicted in FIGS. 6A-6D differ with respect to the design and construction of the elastic segment 44 discussed above.

In FIG. 6A, a segment of the outer housing has been replaced by an elastic membrane 71. In FIG. 6B, the elastic membrane has been divided into a series of wedge-shaped elements 72. The relatively inflexible, inelastic segments 74 interposed between the elastic elements provide structural support and prevent axial expansion during pressurization of channel 50. In FIG. 6C, the wedge-shaped elements have been replaced by a series of kerfs 76, each composed of a par of planar elements 77. In this embodiment the catheter is constructed such that the angle 78 described by the junction of the pair of planar surfaces is controlled by the perator by adjusting the pressure within channel 50. Pressurization of channel 50 will cause the kerfs to unfold, and the planar surfaces of each kerf will contribute more to the outer surface of catheter 20 along the circumferential aspect of the preshaped curve 46 relative to the previous depressurized circumstance. Unfolding of the kerfs thus enhances the disparity in length between the inner 52 and outer 51 (see FIG. 5) of catheter 20 in the region of curve 46.

FIG. 6D illustrates another embodiment of the catheter wherein the kerfs have been replaced by a thin film 80 of a flexible inelastic material capable of withstanding very high pressures, such as mylar. Each wedge is constructed using excess film to permit elongation of surface 51 relative to surface 52 (see Fig.5) during pressurization of channel 50.

FIGS. 7A and 7B illustrate the means by which air is vented from the catheter during infusion of fluid within channel 50. If air were contained within this channel, it could escape in the event of a rupture and embolize within the bloodstream. Furthermore, the presence of air compromises the function of the stiffening element. Hence for both safety and performance, air is vented from channel 50 during infusion of the fluid. This is accomplished by two venting ports 82 which extend along nearly the entire length of the catheter. These venting ports communicate with the lumen of channel 50 at the very distal aspect of the catheter by means of channel 84. During the infusion of fluid in channel 50, these veining ports 82 allow air to be displaced until the entire channel 50 is fluid filled. Fluid leaking out of the vent ports notifies the operator that the channel is entirely vented. Valve 64 then is closed to prevent further loss of fluid (as well as loss of hydrostatic pressure) during subsequent use of the catheter through the venting ports.

FIGS. 8A-8F illustrate other embodiments of my catheter. In this embodiment a second eccentrically disposed channel 54 is provided which is coupled to syringe 55 by communicating channel 56. In the same manner as channel 550, channel 54 contains an elastic segment 61 and may be pressurized from outside the patient. Secondary channel 54 enables selective deflection of the distal end 32 of the catheter 20 to assist in positioning the catheter within the coronary artery. It should be understood that any one of the various embodiments of the flexible, elastic segment of channel 50 (depicted in FIGS. 6A-6D) may be employed in segment 61 of channel 54. By placing the secondary channel on catheter 20 at about 0° or 90° rotation from the preshaped curve 46 (and from the orientation of channel 50), as illustrated i FIGS. 8B and 8C respectively, the distal end of the catheter may be deflected inferior or posteriorly (see FIG. 8C) to aid subselective cannulization of the LAD and circumflex branches of the left coronary system, respectively. Channel 83 functions as the vent port for channel 54.

The foregoing has been a description of the preferred embodiments of the invention. Although many specific details have been described, it should be understood that the description is only for the purposes of explaining the invention, and not limiting it. It should be further understood that the configuration of the catheter proposed herein is not limited to the left Judkin's configuration alone. This configuration was selected for the purpose of illustration only. The scope of the invention may be ascertained from the appended claims.

I claim:

1. A catheter comprising:
   an elongate housing having an opening extending from a proximal end to a distal end of its length; and
   controllable stiffening means coupled to a substantially stiffenable portion of the length of the elongate housing to provide at least a first higher flexibility of said substantially stiffenable portion of the elongate housing and a second lower flexibility of said substantially stiffenable portion of the elongate housing as selected by a user of the catheter, the controllable stiffening means comprising a primary chamber having at least a first wall portion and a second wall portion and adapted to be filled with a fluid, which chamber is eccentrically disposed around the elongate housing along said substantially stiffenable portion of the length, said first wall portion being formed by a portion of said elongate housing, wherein when said chamber is filled with a fluid, said second wall portion is elongate with respect to said first wall portion.

2. A catheter as in claim 1 further comprising a channel extending from the primary chamber to the proximal end to permit pressurization of the primary chamber.

3. A catheter as in claim 2 wherein the primary chamber comprises a cylindrical member disposed around the elongate housing and affixed thereto along a portion of the length of the primary chamber.

4. A catheter as in claim 2 wherein an outer surface of the primary chamber is capable of asymmetric elongation when subjected to hydrostatic pressure, resulting in the development of torque.

5. A catheter as in claim 1 wherein the first higher flexibility causes the catheter to assume a bent configuration.

6. A catheter as a claim 5 wherein the bent configuration is a configuration adapted for manipulating the catheter in a position suitable for the performance of percutaneous coronary angioplasty.

7. A catheter as in claim 1 wherein the said substantially stiffenable portion of the length comprises a region in closer proximity to the distal end than to the proximal end.

8. A catheter as in claim 1 wherein the primary chamber includes at least one kerf therein to allow a sharper radius of curvature at that location.

9. A catheter as in claim 1 wherein the primary chamber includes a region of elastic material to allow a sharper radius of curvature at that location.

10. A catheter as claimed in claim 1, wherein the primary chamber includes:
   at least two elastic segments; and
   at least one inelastic segment interposed between said two elastic segments.

11. A catheter, as claimed in claim 1, wherein:
   said second wall portion comprises a sufficient amount of substantially inelastic material to permit said elongation with respect to said first wall portion.

12. A catheter, as claimed in claim 1, wherein:
   said second wall portion includes at least one wedge-shaped portion of elastic material.

13. A catheter, as claimed in claim 2, further comprising:
   means or venting air from said catheter when fluid is infused in said channel.

14. A catheter, as claimed in claim 2, further comprising:
   a longitudinally extending port configured for venting air when fluid is infused in said channel.

15. A catheter, as claimed in claim 14, further comprising:
   valve means for controlling flow through said port.

16. A catheter, as claimed in claim 14, further comprising:
   means for venting air from said catheter when fluid is infused in said secondary channel.

17. A catheter, as claimed in claim 13, wherein said secondary chamber is disposed at a predetermined angle with respect to said primary chamber to permit deflecting the distal portion of said catheter.

18. A method, as claimed in claim 17, further comprising:
   venting air from said catheter.

19. A catheter comprising:
   an elongate housing an opening extending from a proximal end to a distal end of its length;
   controllable stiffening means coupled to a portion of the length of the elongate housing to provide at least a first higher flexibility of that portion of the elongate housing and a second lower flexibility of that portion of the elongate housing as selected by a user of the catheter, the controllable stiffening means comprising a primary chamber adapted to be filled with a fluid, which chamber is eccentrically disposed around the elongate housing along the portion of the length;
   a channel extending from the primary chamber to the proximal end to permit pressurization of the primary chamber; and
   a secondary chamber disposed along the elongate housing more proximal to the distal end than the primary chamber.

20. A catheter as in claim 19 further comprising a secondary channel extending adjacent the opening of the elongate housing from the proximal end and coupled to the secondary chamber to permit pressurization thereof.

21. A catheter as in claim 20 wherein the secondary chamber is positioned axially offset from the primary chamber.

22. A catheter as in claim 21 wherein an outer surface of the secondary fluid-filled chamber is capable of asymmetric elongation when subjected to hydrostatic pressure resulting in deflection of the tip of the catheter.

23. A catheter comprising:
   an elongate housing having an opening extending from a proximal end to a distal end of its length;
   controllable stiffening means coupled to a portion of the length of the elongate housing to provide at least a first higher flexibility of that portion of the elongate housing as second lower flexibility of that portion of the elongate housing and a selected by a user of the catheter, the controllable stiffening means comprising a primary chamber adapted to be filled with a fluid, which chamber is eccentrically disposed around the elongate housing along the portion of the length; and
   an angioplasty dilation catheter disposed within the opening.

24. A method for performing an angioplasty procedure using a guiding catheter having controllable stiffening means comprising a primary chamber adapted to be filled with a fluid which chamber is eccentrically disposed around the guiding catheter and affixed to a portion of the guiding catheter in proximity to the distal end comprising:
   introducing the guiding catheter to a desired position within a patient;
   employing the controllable stiffening means to increase the rigidity of the portion of the catheter to which the controllable stiffening means is affixed;
   performing the angioplasty procedure;
   employing the controllable stiffening means to reduce the rigidity of the portion of the catheter; and
   removing the catheter.

* * * * *